(12) United States Patent
Chava et al.

(10) Patent No.: US 7,272,406 B2
(45) Date of Patent: Sep. 18, 2007

(54) SYSTEM AND METHOD FOR IN-TRANSIT SMS LANGUAGE TRANSLATION

(75) Inventors: Venkatesh Chava, Herndon, VA (US); Mark R. Smith, Warrenton, VA (US); William H. Dudley, Addison, TX (US)

(73) Assignee: Sybase 365, Inc., Chantilly, VA (US)

( * ) Notice: Subject to any disclaimer, the term of this patent is extended or adjusted under 35 U.S.C. 154(b) by 835 days.

(21) Appl. No.: 10/607,981

(22) Filed: Jun. 30, 2003

(65) Prior Publication Data
US 2004/0266462 A1    Dec. 30, 2004

(51) Int. Cl.
*H04Q 7/20* (2006.01)
*H04M 3/42* (2006.01)

(52) U.S. Cl. ............... 455/466; 379/201.01; 455/414.1

(58) Field of Classification Search ............... 455/466, 455/414.1; 379/201.01, 201.02
See application file for complete search history.

(56) References Cited

U.S. PATENT DOCUMENTS

| | | | |
|---|---|---|---|
| 5,351,235 A | | 9/1994 | Lahtinen |
| 5,371,732 A | | 12/1994 | Brocken et al. |
| 5,384,831 A | * | 1/1995 | Creswell et al. ........ 379/114.05 |
| 5,524,137 A | * | 6/1996 | Rhee ...................... 379/88.01 |
| 5,621,727 A | | 4/1997 | Vaudreuil |
| 5,768,509 A | | 6/1998 | Gunluk |
| 5,887,249 A | | 3/1999 | Schmid |
| 5,894,478 A | | 4/1999 | Barzegar et al. |
| 6,052,458 A | | 4/2000 | Amir-Ebrahimi |
| 6,208,870 B1 | | 3/2001 | Lorello et al. |
| 6,230,004 B1 | * | 5/2001 | Hall et al. ............... 455/414.2 |
| 6,230,009 B1 | | 5/2001 | Holmes et al. |
| 6,240,293 B1 | | 5/2001 | Koster |
| 6,327,267 B1 | | 12/2001 | Valentine et al. |
| 6,366,663 B1 | | 4/2002 | Bauer et al. |
| 6,421,437 B1 | | 7/2002 | Slutsman |
| 6,512,448 B1 | * | 1/2003 | Rincon et al. ............. 340/7.51 |
| 6,535,746 B1 | | 3/2003 | Yu et al. |

(Continued)

FOREIGN PATENT DOCUMENTS

EP    0 777 394 A1    12/1995

(Continued)

OTHER PUBLICATIONS

International Search Report & Written Opinion, Feb. 27, 2007.

*Primary Examiner*—Harry S. Hong
(74) *Attorney, Agent, or Firm*—Edell, Shapiro & Finnan, LLC

(57) ABSTRACT

A system and method for facilitating electronic communication between people who speak different languages. An SMS message including content in a first language is received at a network node. It is then determined whether the content of the SMS message is to be translated to a second language before being sent to a recipient. This determination can be based on an embedded code or an the fact that a bounded session has been previously established. The content is then translated from the first language to the second language, and the SMS message is thereafter sent to the recipient directly from the network node at which the translating step was performed.

26 Claims, 3 Drawing Sheets

U.S. PATENT DOCUMENTS

| | | |
|---|---|---|
| 6,560,226 B1 | 5/2003 | Torrey et al. |
| 6,594,254 B1 | 7/2003 | Kelly |
| 6,633,764 B1 | 10/2003 | Garcia |
| 6,658,260 B2 | 12/2003 | Knotts |
| 6,738,630 B2 | 5/2004 | Ashmore |
| 6,772,267 B2 | 8/2004 | Thaler et al. |
| 2002/0015403 A1 | 2/2002 | McConnell et al. |
| 2002/0029189 A1 | 3/2002 | Titus et al. |
| 2002/0112014 A1 | 8/2002 | Bennett et al. |
| 2002/0167909 A1 | 11/2002 | Balazinski et al. |
| 2003/0078033 A1* | 4/2003 | Sauer et al. ............... 455/466 |
| 2003/0083078 A1 | 5/2003 | Allison et al. |
| 2003/0118027 A1 | 6/2003 | Lee et al. |
| 2003/0125054 A1* | 7/2003 | Garcia ..................... 455/466 |
| 2003/0202521 A1 | 10/2003 | Havinis et al. |
| 2004/0032856 A1 | 2/2004 | Sandstrom |
| 2004/0102201 A1* | 5/2004 | Levin ........................ 455/466 |
| 2004/0192258 A1* | 9/2004 | Atkin et al. ............. 455/412.1 |

FOREIGN PATENT DOCUMENTS

| | | |
|---|---|---|
| EP | 0 959 600 A1 | 4/1999 |
| WO | WO97/36434 | 3/1996 |
| WO | WO97/20442 | 11/1996 |
| WO | WO99/11078 | 8/1998 |
| WO | WO99/33226 | 12/1998 |
| WO | WO 00/41533 | 1/2000 |
| WO | WO 02/25875 A1 | 9/2001 |
| WO | 02/071234 | 9/2002 |

* cited by examiner

SYSTEM AND METHOD FOR IN-TRANSIT SMS LANGUAGE TRANSLATION

BACKGROUND

1. Field of the Invention

The present invention relates generally to SMS messaging and more particularly to systems and methods for enabling cross language communication via SMS messaging.

2. Background of the Invention

Electronic messaging has seen explosive growth in the past few years. As wireless network coverage has expanded and the cost of messaging devices have fallen, business people as well as casual users have increasingly turned to electronic messaging to communicate with one another. One of the messaging techniques that has seen an acute spike in growth is messaging using cellular or mobile telephones. Cellular telephone networks around the world support a protocol that is commonly referred to as the short message service (SMS). SMS messages are typically limited in size to 160 characters and can be easily sent to and from mobile telephones. Addressing is based on the telephone number of the wireless/mobile/cellular telephone.

Because SMS is supported by virtually all of the mobile telephone service providers around the world, there is now the opportunity to support simple and inexpensive messaging between people in different parts of the world. Unfortunately, however, such communication can sometimes be strained by differences in languages. For example, it may be difficult (or even impossible) for an English-only speaker to engage in an SMS messaging session with a French- or German-only speaker without some sort of intervening translation service. One known translation technique that can be used in the context of SMS messaging is the independent translation and transmission method.

In this known method an originator generates an SMS message in a first language with the intent of sending the message to an intended recipient in a second language. In accordance with the known method, the originator generates the message and sends the message to a dedicated application that is accessed by addressing the message to a so-called "short code," (e.g., "3042"). The dedicated application translates the message to the second language and sends back the translated message to the originator. The originator then forwards the translated message to the intended recipient using normal SMS messaging procedures.

The foregoing method has several disadvantages. First, translation and transmission are independent. More specifically, it takes two operations on the part of a user to send a message—a first transmission to a short code and a second transmission to the ultimate destination.

Second, in some cases it may not be possible for the originating mobile phone to receive and display the translated message correctly as a mobile phone typically supports one or few character sets. Accordingly, it is likely that some language translations cannot be supported using this technique.

Third, there is a substantial delay in originating and sending a translated message since multiple messages must be sent and there may be a delay in the response time in forwarding the translated message.

Thus there is a need for improved translation services in the context of electronic messaging and, in particular, SMS messaging.

BRIEF SUMMARY OF THE INVENTION

In accordance with the present invention there are provided several embodiments to implement in-line SMS message language translation. In a preferred embodiment, an intermediary that has pre-existing relationships with wireless service providers, and may be a separate entity in the corporate sense, is configured to receive an SMS message and scan that message for an embedded code. The code may be embedded in the content portion of the message or in the address portion of the message and preferably identifies at least the language to which the content of the SMS message is to be translated. An exemplary embedded code might be *34#, which might represent a request to translate the content of the message from English to German.

Once the message is translated, using well-known automated text translating systems, the message is forwarded directly to the intended recipient, thereby avoiding the disadvantage of prior art translation systems that sent the translated message back to the originator for subsequent forwarding. In other words, the translation of the SMS message in accordance with the present invention is "in-line" in the sense that from the users' point of view the message has been sent from the originator and received by the recipient without extra steps.

In another embodiment of the present invention a session is established during which all messages being sent are translated to a desired language before being forwarded to the intended recipient. The session can be set with a time-out period or be indefinite. An advantage of this embodiment is that a user need not be bothered, during each message send operation, to remember to expressly request or indicate that translation of the message is desired.

The foregoing and other aspects of the present invention and their attendant advantages will be more fully appreciated upon reading the following detailed description in conjunction with the associated drawings.

DETAILED DESCRIPTION OF THE INVENTION

Figure 1:
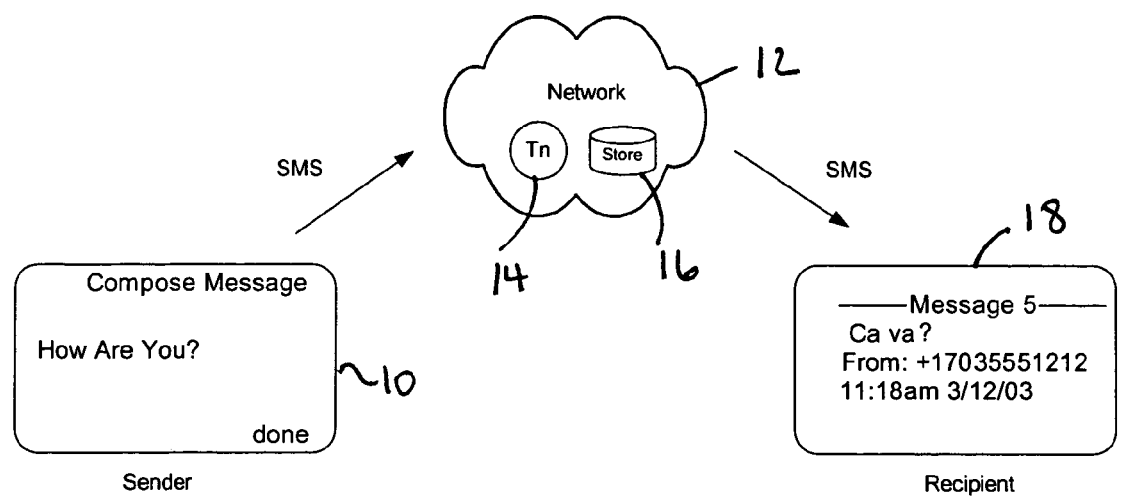
FIG. 1 shows exemplary SMS message flow in accordance with the present invention.

An SMS message is typically characterized by originating phone number, destination phone number and content. In the case of Peer to Peer messaging, an SMS message is typically originated in a mobile phone. All SMS messages go through at least one message center called a short message service center (SMSC). In some networks, notably GSM, the home SMSC (i.e., the SMSC of the service provider with which an originator is associated with) is always involved in SMS transmission. The SMSC receiving the message forwards the message to the destination either directly or through other SMSCs.

The present invention is directed to a scheme to enable in-line coded SMS language translation. The present invention provides a mechanism for initiating translation of an SMS message during transit from the originator to the intended recipient based on an embedded code associated with the transmission of a mobile-originated SMS message. The translation from one language to another is carried out based on explicit command by the initiator of the SMS text message. The command preferably includes information about both source and target languages. In some cases the command may simply include only the target language, if source language is identifiable by looking at the content.

Typically, each SMS message is considered as an independent message by the network facilitating the transmission. However, in accordance with the present invention, it is possible to establish a virtual session for the purpose of language translation using session oriented commands for translation, as further explained below.

While individual messages can be commanded for translation, this may not be convenient in a SMS based chat session. In such a scenario, a session is preferably established by first sending a command to a special short code (a short code is a special destination number, typically 3 to 6 digits, that represents a messaging application or service provider). The content of the message destined for the short code contains the destination phone number and the command for translation. Once the session is established, all the messages from the originating telephone number to the destination telephone number are translated as desired. If the command is to translate messages from, e.g., English to French, then all the messages are converted. In a preferred implementation, there is a session time out and the session gets refreshed after every message exchanged between the two parties concerned.

Preferably a session can be established by both the parties independently in order to avail this feature. This means that it is possible for a receiving party to send a command that instructs the network to translate messages coming from a specific sender for the duration of a session.

Another variation of the session concept is to set up an infinite session that is maintained until the user cancels the command. Thus, translation between two identified entities is in continuous effect during this time.

In still another variation, the destination subscriber registers with a short code (or long code as described later) to the central translation provider with information that indicates the telephone number, and in the content of the message, his language preferences such as originating country code. From that point on, all messages sent from that country code to his handset can be translated. Conversely, the originating subscriber can register so that all messages originating from him, destined to specific country codes may be translated.

In either case, single message or session messaging, FIG. 1 shows the fundamental in-line SMS message translation message flow in accordance with the present invention. As shown, an SMS message 10 is composed by a sender who then sends the message to a recipient. Message 10 passes through network 12, which is typically comprised of at least a network segment belonging to a wireless telephone service provider. Network 12 preferably includes a translating module Tn 14, which is responsible for generating actual language translation, and a store 16 or database that stores look up tables for words, short and long codes, preferences etc., and is responsible for forwarding the translated message 18 to a recipient.

Coding Customer Intent

A user's intent to translate a message while in transit to the destination can be coded in a variety of different ways in accordance with the present invention. As will be explained in more detail below some ways may be more advantageous than others in terms of user experience and routing.

In-line Coding

This technique refers to embedding a code in line with the content of the SMS text message. In order to distinguish the coded intent from other content, the code is preferably unique and should preferably not be repeated as part of regular content. Usually, the first word of the content portion of an SMS message is reserved for embedding the code as it is generally accepted to be more user friendly than embedding the code in the middle or end of the content. Also, embedding a code at the end of the message may be problematic if, for any reason, the message is truncated or split into multiple messages. In reality, truncation and/or splitting does occur in the course of SMS messaging as a message traverses multiple networks due to differences in the length of messages and protocols supported by those networks.

Coding Techniques

Typically, an SMS message encoded using the Latin character set is 160 characters (7 bit characters) or 140 characters (octets) long. However, the length of a message encoded using the Unicode character set is 69 characters at most. A code (for language translation or other features) should usually take as few characters as possible in order to leave maximum space for the rest of the message. At the same time, the code should be intuitive enough for users to remember easily.

In a preferred embodiment of the present invention an Intermediary is involved in providing the translation service. In this case, such an Intermediary would be located within network 12, but would be transparent to users. In a preferred implementation, such an Intermediary is connected to more than one carrier, possibly across the continents and is preferably a separate entity in the corporate sense. Thus, an easily coded universal symbol is preferably employed to codify the customer intent inline with the message. Two buttons with symbols that are almost universally present are "*" and "#".

By embedding appropriate codes for language translation between these two symbols, many possible codes can be obtained that uniquely represents subscriber intent for translation services.

Examples are:

| | |
|---|---|
| SMS To: | +17035551212 |
| SMS From: | <originator's phone number in e.164 format> |
| SMS Content: | *33#<content> |
| SMS To: | +17035551212 |
| SMS From: | <originator's phone number in e.164 format> |
| SMS Content: | *34#<content> |

Further, the numbers could represent characters on the mobile phone key pad to easily identify the service needed. In the examples above, code 33 might represent English to French translation, while code 34 might represent English to German translation. Numbers may be coded according to the alphabet letters associated with a telephone number key pad.

Alternatively, the code could be alphanumeric characters which are more intuitive to the user. Typically, these codes would be 3–5 characters, excluding the leading "*" or ending "#" as shown in the examples below.

| | |
|---|---|
| SMS To: | 17035551212 |
| SMS From: | <originator's phone number in e.164 format> |

-continued

| SMS Content: | *ef#<content> |
| --- | --- |
| SMS To: | 17035551212 |
| SMS From: | <originator's phone number in e.164 format> |
| SMS Content: | *ec#<content> |

In the above examples, *ef# code represents English to French translation and *ec# represents English to Chinese translation.

The in line coding of the present invention is advantageous in several ways. For example, no explicit network routing support from originating network operators is needed. Also, arbitrarily long inline codes (subject to length restrictions of SMS messages) can be supported. Therefore, translation codes that are relatively easy to remember can be devised and employed. Further, regular SMS exchange is supported transparently in that an SMS message can be sent using the terminating mobile phone number. Further still, in line coding works in a roaming scenario. Finally, there is identical user experience irrespective of origination of message as the coding is common across the networks, as long as the same service provider is involved for translating the message.

On the other hand it is noted that with in line coding there is a slight loss of available characters that could otherwise be used for content and, depending on the actual implementation, there could be wasted processing power and latency since every message may need to be scanned for the embedded code.

In addition, there is the possibility of "false positives" where the code could appear naturally as part of the message itself, but be interpreted as being an in line code to trigger translation. Likewise, those skilled in the art will appreciate that many SMSCs support "scan codes" whereby the 1st characters of the message content, beginning with a special character, such as a "*" or "#" may be used to control some element of the SMS platform. Thus, any in line coding in accordance with the present invention is preferably compatible with various scan codes that SMSCs might deploy. That is, the intermediary (if one is employed), and the carriers involved should coordinate among themselves as to how best to avoid the foregoing issue.

Short Number Coding

A short number can be used for routing the SMS message. Since some short codes can be used themselves for routing in an SMS network system, both the intent (of language translation facility) and routing information can be embedded in one code. The short number (also referred to herein as a short code) is used for routing the message to an application hosted, perhaps, by a value added service provider, such as the Intermediary mentioned previously. However, in order to keep the translation service "in-line" with the actual SMS conversation itself, it is necessary to forward the message after translation to the intended recipient. Since the "To" field in the originated SMS message is used in this embodiment for routing to the translation application (14 in FIG. 1), the message itself must be embedded with the recipient phone number in some coded format. Again, a similar coding mechanism using "*" and "#" keys can be used to embed the phone number as follow:

| SMS To: | 3400 |
| --- | --- |
| SMS From: | <originator's phone number in e.164 format> |
| SMS Content: | *+17035551212#<content> |

Here, the short code is: 3400. Again, depending upon the originating operator's availability of short codes, the code itself can be encoded so that the translation associated with the code can be remembered easily. In this example, 3400 could imply translation from English to German language as numbers 3 and 4 represent 'e' and 'g' characters respectively.

The messages routed to the short code are received by the inter-carrier SMS network provider (Intermediary) that translates the message and forwards the message to the recipient phone number embedded in the message itself.

One implementation of short code could use a single, common short code (common across a wide variety of carriers) that would function as a language translation clearinghouse. In this scenario, the subscriber would send a message to be translated to the single short code with the required language and the destination number of the recipient. For example:

| SMS To: | 5000 |
| --- | --- |
| SMS From: | <originator's phone number in e.164 format> |
| SMS Content: | *+17035551212*FR#<content> |

In the above example *FR# represents translation to French language. In this scenario, there is some additional loss of content and the recipient must also go through the short code to have the message translated back when the recipient responds.

A significant advantage of short number coding as described above is that only messages intended for language translation functionality are routed to the language translation application as the short code provides both the intent and routing functionality together.

On the other hand, short number coding may not be intuitive as the message generated is addressed to a short code instead of the intended recipient. Also, there is relatively greater loss of content space as the destination telephone number needs to be embedded in the message content itself. Further, roaming could be an issue if the short code is not properly supported in roaming areas. Also, if the recipient is in another country, he/she would likely not be able to respond to the short code, as this violates international dialing rules, unless the short code was supported in the recipient's country. Finally, billing might be an issue as the foregoing method deviates from "normal" routing.

Long Number Coding

The recipient's telephone number itself could be used to encode subscriber's intent to perform language translation while the message is in transit to the destination. This can be done in a number of ways, depending upon the support from the message originating carrier. The long number is the e.164 formatted telephone number itself which is used for message routing. This long number can be either preceded or appended with a code that is used to divert the message to a language translator application. In a preferred implementation, the extra digits can be stripped off before the message is transmitted to the intended recipient.

| | |
|---|---|
| SMS To: | *123*7035551212 |
| SMS From: | <originator's phone number in e.164 format> |
| SMS Content: | <content> |
| | Appended code |
| SMS To: | 7035551212 34 |
| SMS From: | <originator's phone number in e.164 format> |
| SMS Content: | <content> |

The advantages of long number coding include the fact that only messages intended for language translation functionality are routed to the language translation application as the long code provides both the intent and routing functionality together, as well as the fact that telephone number and intent are coded in the same number, thereby increasing efficiency.

Possible disadvantages of long number coding include the requirement for all network elements to correctly interpret the routing in the presence of extra digits, the possibility that support from roaming partners may be problematic in certain instances, especially if an intermediate SMSC happens to process the messages, billing might be an issue as the method deviates from "normal" routing, and long codes might be different in different networks and therefore there may not be a uniformity in service.

Message Center Based Coding

In some networks, notably GSM, it is possible for the originator of the SMS message to specify an SMSC to which the message is to be routed for onward transmission. In accordance with the present invention, for all messages meant for language translation, a special SMSC can be designated. There are two cases that should be addressed here to unambiguously identify the intended language.

SMSC Number Based Coding: It is possible to have one SMSC number for each destination language type. This technique assumes that the source language is identifiable using the content. The disadvantage of this technique is that the user has to know the SMSC number for each destination language.

In-Line Coding: This technique, explained previously, embeds a code inside the content to identify the source and destination languages. The advantage of In-Line coding in association with SMSC coding (in contrast to the previously described In-Line coding technique) is that only messages meant for translation go to an SMSC, which examines the content to understand the user intent.

Reverse Transcoding and Ambiguity Resolution

When an SMS message is originated for language translation, the user may want to see a copy of what was translated. While a translated copy can be sent back to the original user no useful purpose is served if the user cannot read the translated version, which is the reason why the message was requested to be translated in the first place. In addition to this obvious problem, some originating phones may not be equipped to receive message in some languages.

One way to overcome the above problem is to perform a reverse translation of the translated message back into the original language and send the thus-translated SMS message to the originator. It is well understood that each translation may corrupt the semantic meaning of the message and reverse translation may not represent the original message or even the translated message well. Nevertheless this technique can be used and works reasonably well in many cases.

Figure 2:
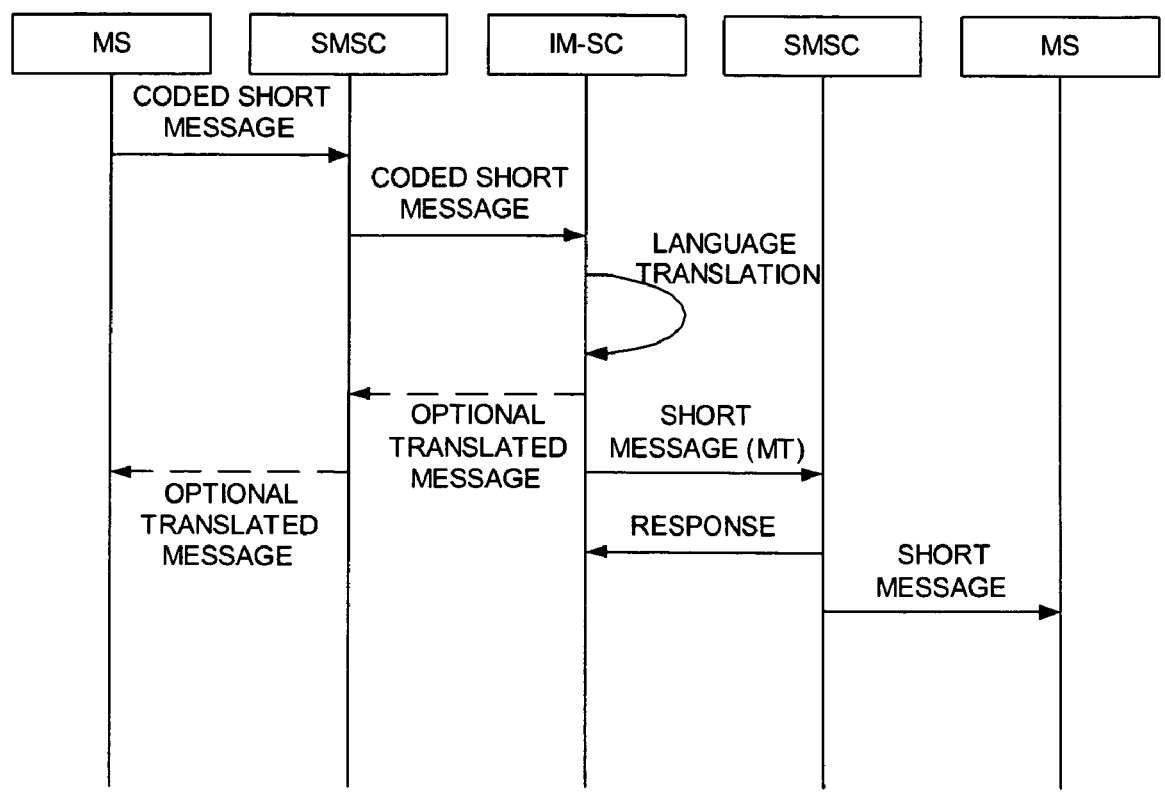
FIG. 2 shows an exemplary SMS message exchange in accordance with the present invention.

FIG. 2 shows an exemplary SMS message exchange in accordance with the present invention. Specifically, a coded short message is sent from a mobile subscriber (MS) to a short message service center (SMSC). From there, the coded short message, in response to the embedded code, is forwarded to an application that performs translation in accordance with the principles of the present invention. The application in this case is located at an intermediary service center (IM-SC) at which the language translation of the coded short message is completed.

Optionally, as described above, the translated message is returned to the originating SMSC whereupon it is forwarded to the originator. As also explained above, the translated message may also be re-translated back to the originating language if desired.

Meanwhile, the translated short message is forwarded to the intended recipient's SMSC, which is programmed to send an acknowledgement response back to the forwarding agent, in this case the IM-SC. The intended recipient's SMSC then forwards the translated short message to the intended recipient.

Figure 3:
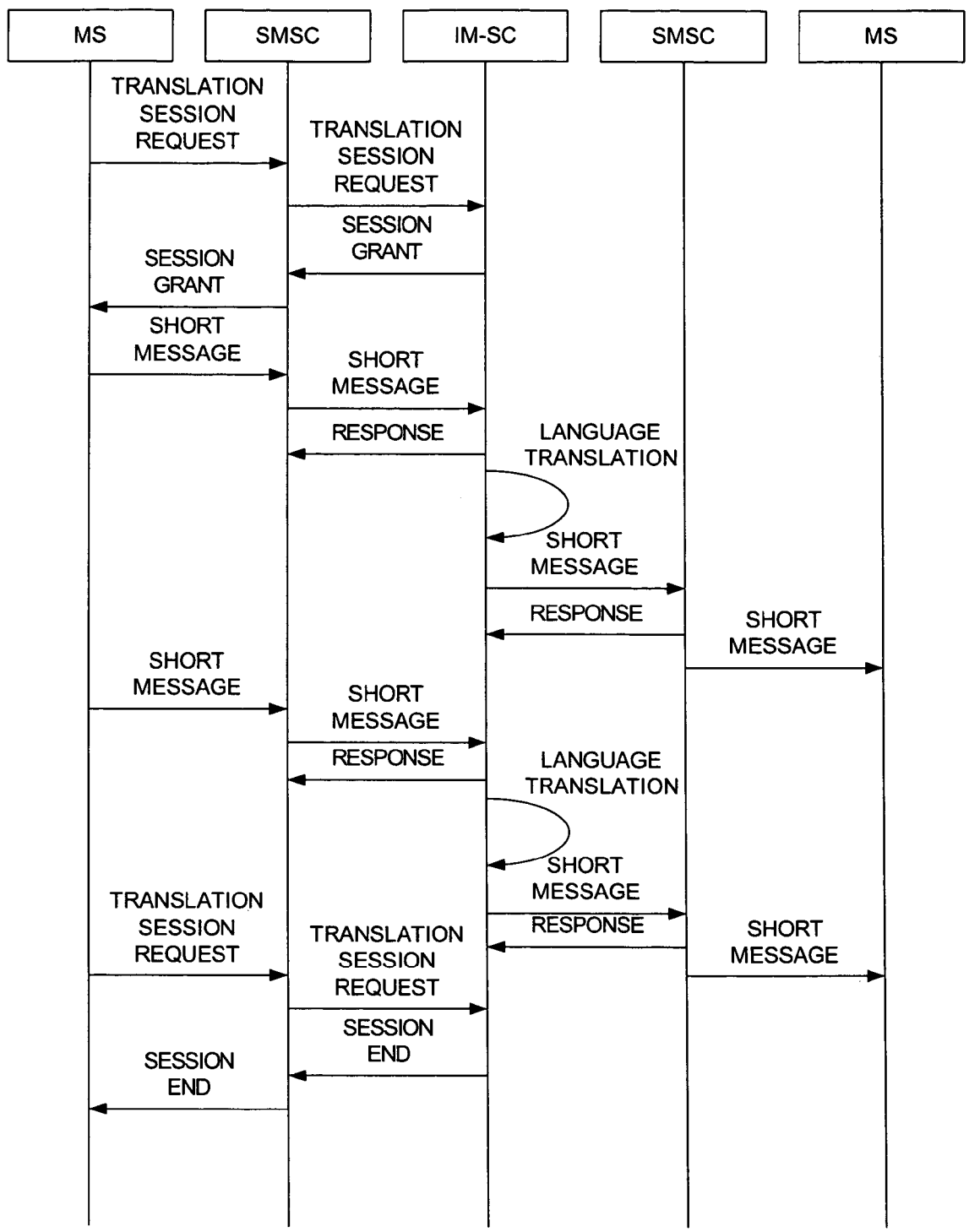
FIG. 3 shows an exemplary commanded session bound SMS message exchange in accordance with the present invention.

FIG. 3 shows an exemplary commanded session bound SMS message exchange in accordance with the present invention. As shown in FIG. 3, a translation session request is sent from the originator to the originator's SMSC. That request is then forwarded to the IM-SC. The IM-SC returns a session grant response to the SMSC that is then forwarded to the message originator. Thereafter, the originator can send messages that will subsequently be translated in accordance with the principles of the present invention and as explained, for example, with respect to FIG. 2. Ultimately, after one or more messages have been sent and the user elects to end the translation session, the originator again sends a translation session request to the originator's SMSC. The originator's SMSC then forwards this request to the IM-SC which may, for example, reset a translation functionality flag and cause a session end command for acknowledgement to be sent to the originator's SMSC. The originator's SMSC then forwards this session end command to the originator's SMS message generating device.

Thus, FIGS. 2 and 3 depict two basic methods or techniques for effecting SMS message translation. The first is via embedded codes in the SMS message, while the second is via a session-based technique. In either case, messages are translated from one language to another to enable communication between or among people whose second or third language skills may be insufficient to successfully communicate with another person.

Finally it is noted that systems for automatically translating text from one language to another are well-known to those skilled in the art, as is the function of scanning a file, such as an SMS message, for a particular character string to, e.g., locate and decipher an embedded code like those described herein.

In view of the foregoing, those skilled in the art will appreciate the several unique aspects of the present invention. Namely, the present invention provides, among other things, SMS message translation service that is provided "inline" with the conversation almost transparently to the users, virtually all languages can be supported irrespective of the capability of the originating mobile phone in supporting various character sets, and depending upon the network architecture, an independent service provider can provide this service using Message Center coding techniques even though a home network may not support the language translation feature.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for translating an SMS message from a first language to a second language, comprising:
   receiving an SMS message in a first language at a network node;
   scanning the message at the network node for a code embedded in the SMS message, wherein the embedded code identifies, at least in part, the second language into which the SMS message is to be translated;
   translating content of the SMS message from the first language to the second language in accordance with the embedded code resulting in translated content; and
   sending the SMS message to a recipient without sending the SMS message back to an originator, wherein the SMS message includes the translated content.

2. The method of claim 1, wherein the embedded code is a short code.

3. The method of claim 1, wherein the embedded code is preceded by a non-numerical character.

4. The method of claim 1, wherein the embedded code is located in a content portion of the SMS message.

5. The method of claim 1, wherein the embedded code is located in an addressing location of the SMS message.

6. The method of claim 5, wherein the embedded code is positioned adjacent a telephone number.

7. The method of claim 1, wherein the embedded code identifies both the first and second languages.

8. The method of claim 1, wherein the step of translating is performed at an intermediary service provider that is different in a corporate sense from a telecommunication service provider that provides SMS messaging service.

9. The method of claim 1, further comprising re-translating the translated content to the first language and sending the thus re-translated content to an originator of the SMS message.

10. The method of claim 1, further comprising scanning for the embedded code.

11. A method for facilitating electronic communication between people who speak different languages, comprising:
   receiving an SMS message including content in a first language;
   determining whether the content of the SMS message is to be translated to a second language before being sent to a recipient;
   translating at least a portion of the content from the first language to the second language; and
   sending the SMS message with the content translated from the first language to the second language to the recipient directly from a network node at which the step of translating was performed,
   wherein the step of determining comprises scanning the SMS message for an embedded code.

12. The method of claim 11, wherein the embedded code is preceded by a non-numerical character.

13. The method of claim 11, wherein the embedded code is located in a content portion of the SMS message.

14. The method of claim 11, wherein the embedded code is located in an addressing location of the SMS message.

15. The method of claim 14, wherein the embedded code is positioned adjacent a telephone number.

16. The method of claim 11, wherein the embedded code identifies both the first and second languages.

17. The method of claim 11, wherein the step of translating is performed at an intermediary that is different in a corporate sense from a telecommunication service provider that provides SMS messaging service.

18. The method of claim 11, further comprising re-translating the translated content to the first language and sending the thus re-translated content to an originator of the SMS message.

19. A method for translating an SMS message from a first language to a second language, comprising:
   receiving at a network node a request to open an SMS message content translation session;
   receiving an SMS message in a first language at the network node;
   translating the content of the SMS message from the first language to the second language; and
   sending the SMS message with the content translated from the first language to the second language to a recipient directly from the network node at which the step of translating was performed.

20. The method of claim 19, further comprising canceling the translation session.

21. The method of claim 19, wherein the translation session is indefinite.

22. A method for translating an SMS message from a first language to a second language, comprising:
   receiving an SMS message having content in a first language at a user selectable short message service center (SMSC), said user selectable SMSC being operable to translate the content from the first language to a second language;
   translating the content from the first language to the second language; and
   sending the SMS message with the content translated from the first language to the second language to a recipient directly from the user selectable SMSC.

23. The method of claim 22, wherein the user-selectable SMSC is operable to also translate content from the first language to languages other than the second language.

24. The method of claim 22, wherein the user selectable SMSC is dedicated to translating content from the first language to the second language only.

25. The method of claim 24, further comprising offering multiple user selectable SMSCs to subscribers, each one of said multiple user selectable SMSCs respectively being operable to translate between different pairs of languages.

26. A method for translating content of an electronic message from a first language to a second language, comprising:

receiving an electronic message in a first language at a network node;

scanning the electronic message at the network node for a code embedded in the electronic message, wherein the embedded code identifies, at least in part, the second language into which the electronic message is to be translated;

translating content of the electronic message from the first language to the second language in accordance with the embedded code resulting in translated content; and sending the electronic message to a recipient without sending the electronic message back to an originator, wherein the electronic message includes the translated content.

* * * * *